(12) United States Patent
Song et al.

(10) Patent No.: US 8,781,199 B2
(45) Date of Patent: Jul. 15, 2014

(54) HYBRID DUAL-MODALITY IMAGE PROCESSING SYSTEM AND METHOD

(75) Inventors: Xiyun Song, Santa Clara, CA (US);
Angela Da Silva, Danville, CA (US);
Jinghan Ye, Fremont, CA (US); Alicia Wong, Antioch, CA (US); Sudhir K. Mahakali, Cupertino, CA (US);
Jingkun Hu, Dublin, CA (US)

(73) Assignee: Koninklijke Philips N.V., Eindhoven (NL)

( * ) Notice: Subject to any disclaimer, the term of this patent is extended or adjusted under 35 U.S.C. 154(b) by 375 days.

(21) Appl. No.: 13/203,507

(22) PCT Filed: Feb. 9, 2010

(86) PCT No.: PCT/IB2010/050580
§ 371 (c)(1),
(2), (4) Date: Aug. 26, 2011

(87) PCT Pub. No.: WO2010/109342
PCT Pub. Date: Sep. 30, 2010

(65) Prior Publication Data
US 2012/0002857 A1 Jan. 5, 2012

Related U.S. Application Data

(60) Provisional application No. 61/162,692, filed on Mar. 24, 2009.

(51) Int. Cl.
*G06K 9/00* (2006.01)
*A61B 6/03* (2006.01)
*A61B 6/00* (2006.01)

(52) U.S. Cl.
CPC ............... *A61B 6/032* (2013.01); *A61B 6/037* (2013.01); *A61B 6/5235* (2013.01)

USPC .......................................... 382/131; 382/294

(58) Field of Classification Search
USPC .................. 382/100, 128–132, 294
See application file for complete search history.

(56) References Cited

U.S. PATENT DOCUMENTS

| 5,210,421 | A | 5/1993 | Gullberg et al. |
| 5,672,877 | A | 9/1997 | Liebig et al. |
| 6,631,284 | B2 | 10/2003 | Nutt et al. |
| 7,507,968 | B2 * | 3/2009 | Wollenweber et al. .. 250/363.07 |
| 8,077,943 | B2 * | 12/2011 | Williams et al. .............. 382/128 |

(Continued)

OTHER PUBLICATIONS

Weigert, M., et al.; Whole-body PET/CT imaging: Combining software-and-hardware-based co-registration; 2008; Z. Med. Phys.; 18(1)59-66.

*Primary Examiner* — Shefali Goradia

(57) ABSTRACT

Hybrid dual-modality image processing systems and methods are disclosed. For example, an image processing system includes a computer for processing SPECT tomographic projection data and a CT volume image. The computer derives a SPECT transverse volume image from the projection data and registers the SPECT transverse volume image with the CT volume image to obtain an attenuation map and registration information. The computer uses the attenuation map and the registration information to derive a SPECT transverse volume image with attenuation correction. The computer uses the registration information to derive a SPECT transverse volume image without attenuation correction. The SPECT transverse volume images, with and without attenuation correction, are derived at or near the same time, using the same registration information. The registration information is stored in, carried by, or otherwise communicated through the attenuation map for subsequent processing of the SPECT transverse volume images.

32 Claims, 10 Drawing Sheets

(56) References Cited

U.S. PATENT DOCUMENTS

Figure 1A:
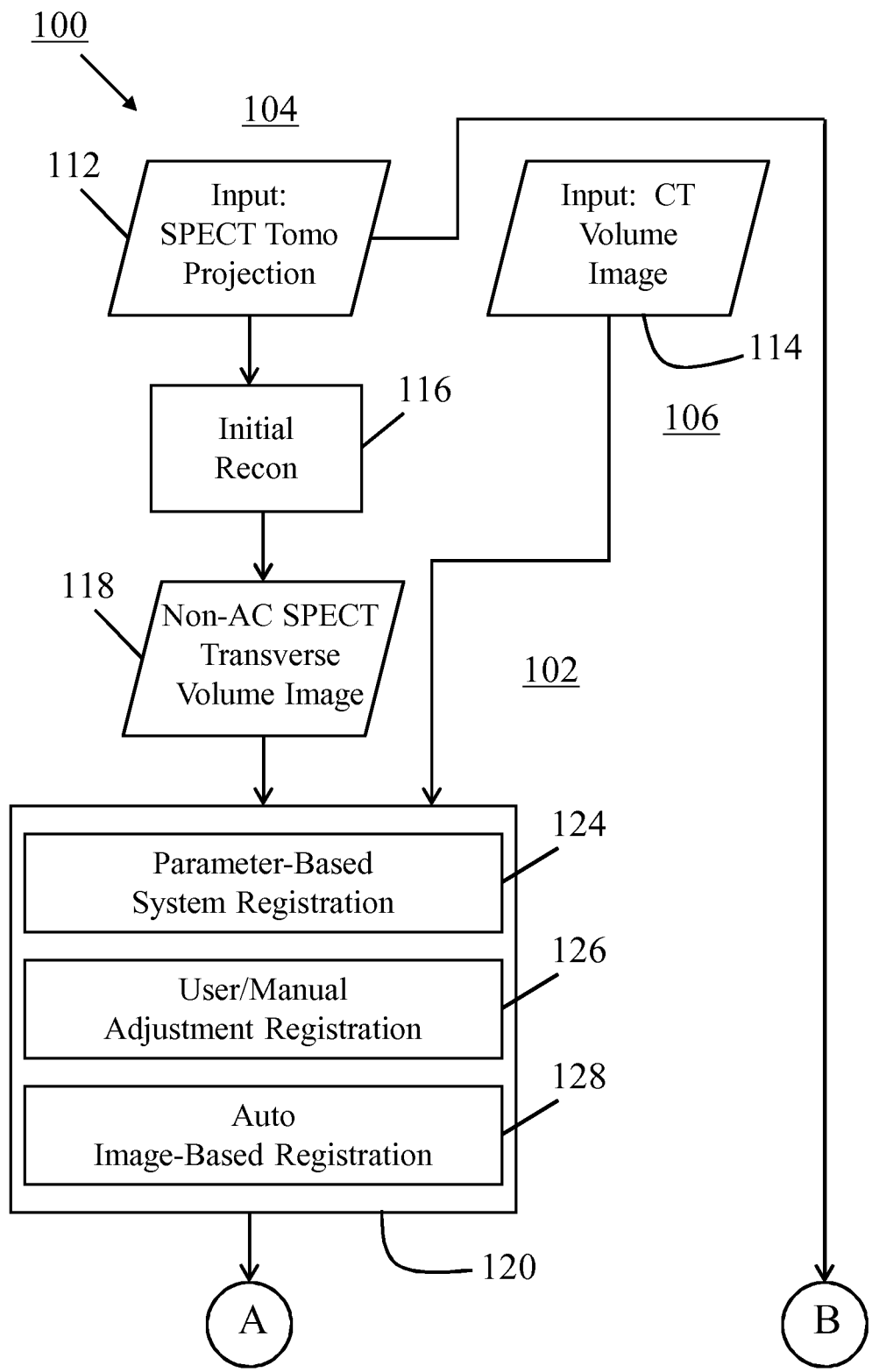

| | | | |
|---|---|---|---|
| 8,108,024 B2 * | 1/2012 | Carlsen et al. | 600/407 |
| 8,611,628 B2 * | 12/2013 | Hu et al. | 382/131 |
| 2007/0003014 A1 * | 1/2007 | Boese et al. | 378/95 |
| 2007/0131858 A1 | 6/2007 | Wollenweber et al. | |
| 2008/0107229 A1 | 5/2008 | Thomas et al. | |
| 2009/0012383 A1 | 1/2009 | Virtue et al. | |
| 2011/0081067 A1 * | 4/2011 | Ye et al. | 382/131 |

\* cited by examiner

HYBRID DUAL-MODALITY IMAGE PROCESSING SYSTEM AND METHOD

CROSS REFERENCE TO RELATED APPLICATIONS

This application claims the benefit of U.S. provisional application Ser. No. 61/162,692 filed Mar. 24, 2009, which is incorporated herein by reference.

The present application relates to medical imaging systems and methods. It finds particular application in dual-modality image processing systems and methods and their related workflows.

Single photon emission computed tomography (SPECT) is a nuclear medicine tomographic imaging technique using gamma rays. SPECT is able to provide true three-dimensional (3-D) imaging information. This 3-D imaging information is typically presented as cross-sectional (i.e., transverse) slices through a patient, but can be freely reformatted or manipulated as required.

In SPECT imaging, a radioactive tracer is administered to the patient and gamma radiation emitted by the tracer is measured. In particular, the gamma radiation is measured using a gamma camera to acquire multiple two dimensional (2-D) images, which are also called projections, from multiple angles. For example, the gamma camera is rotated around the patient and projections are acquired at defined points during the rotation, typically every 3-6 degrees.

A computer is then used to apply a tomographic reconstruction algorithm to the multiple projections, yielding a 3-D imaging dataset. This imaging dataset may then be manipulated to show thin slices along any chosen axis of the body, similar to those obtained from other tomographic techniques, such as magnetic resonance imaging (MRI), computed tomography (CT), and positron emission tomography (PET). In general, the resulting reconstructed images will be of lower resolution, have increased noise compared to planar images, and be susceptible to artifacts.

Inherent in SPECT imaging are degradations, which distort the projection data and, thus, the reconstruction based thereon. Artifacts, such as streaking, can arise during SPECT imaging, for example, due to movement of the patient during scanning or due to a highly uneven distribution of a radiopharmaceutical. Furthermore, attenuation of the gamma rays within the patient can lead to significant underestimation of activity in deep tissues, compared to superficial tissues. Attenuation correction (AC) is often obtained with measured attenuation values. Modern SPECT equipment is often sold with an integrated x-ray CT scanner, resulting in a dual-modality system. As x-ray CT images represent a good attenuation map of the tissues, this data can be incorporated into the SPECT reconstruction to correct for attenuation. The x-ray CT data also provides a precisely registered CT image which can provide additional anatomical imaging information.

A SPECT/CT dual-modality system includes both SPECT and CT imaging components to respectively provide physiological and anatomical information for diagnosis or treatment planning. For example, the registration and fusion display of the SPECT and CT images can make it much easier for users (e.g., physicians) to identify and localize suspected defects or tumors for diagnosis.

Since users will often want or need to review these images using third party software, it is desirable to provide registered SPECT and CT volume images that adhere to the DICOM standard. DICOM, which stands for Digital Imaging and Communications in Medicine, is a standard that was developed to aid in the distribution and viewing of medical images. The DICOM standard defines a file format for the distribution of images. A single DICOM file, which contains both a header and all of the image data, can contain information in three dimensions. The header portion includes many predefined attributes that are used to store information on the patient, the type of scan, image dimensions, etc.

The public attributes of "Image Position (Patient)" (IPP) and "Image Orientation (Patient)" (IOP) in a DICOM file header define, respectively, the position and orientation (or direction) of an image relative to the patient space coordinate system. The IPP and IOP attributes can be used to carry registration information between two or more images. For transverse volume images, the IOP attribute has a constant vector value of [1 0 0 0 1 0] according to the DICOM standard, while for other images, the IOP vector can have different values, on a case-by-case basis.

In clinical practice involving SPECT, reoriented images are often used as a matter of convenience, instead of or in addition to the direct use of the transverse images. The reoriented images can include, for example, short-axis, horizontal-long-axis, and vertical-long-axis images for cardiac studies; and oblique transverse, oblique sagittal, and oblique coronal images for non-cardiac studies. When reviewing these derived SPECT images, fusion with CT data can bring significant improvement in diagnosis confidence.

As noted above, the CT data can provide an attenuation map which is useful for attenuation correction (AC) in SPECT reconstruction to achieve more accurate quantification and to reduce attenuation artifacts. However, even when the CT-based attenuation map is available, there may be a need or desire for a user to do SPECT reconstruction without AC (non-AC) because direct (apple-to-apple) comparison between the AC SPECT image and the non-AC SPECT image could provide increased clinical value. The non-AC SPECT reconstruction could be performed separately and in a workflow independent of the CT data. In the SPECT/CT dual-modality system, the AC and non-AC SPECT comparison can further improve the clinical value and diagnosis confidence when fused with the CT image data.

In accordance with one aspect, hybrid dual-modality image processing systems and methods are disclosed. The image processing systems and methods implement improved image processing workflows.

An image processing system according to one exemplary embodiment, includes a computer component (e.g., a computer), a first tomographic projection data generated by a first imaging modality (e.g., a CT system), and a second tomographic projection data generated by a second imaging modality (e.g., a SPECT or PET system). The computer component generates a first reconstructed image data from the first tomographic projection data, and generates a second reconstructed image data from the second tomographic projection data. The computer component registers the second reconstructed image data with the first reconstructed image data to generate an attenuation map and a registration information. The computer component uses the second tomographic projection data, the attenuation map, and the registration information to generate an attenuation-corrected reconstructed image data corresponding to the second imaging modality, and uses the second tomographic projection data and the registration information to generate a non-attenuation-corrected reconstructed image data corresponding to the second imaging modality.

In one exemplary embodiment, the computer component uses the registration information to re-sample the attenuation-corrected reconstructed image data to a coordinate system of the first reconstructed image data to generate a re-sampled attenuation-corrected reconstructed image data corresponding to the second imaging modality, and uses the registration information to re-sample the non-attenuation-corrected reconstructed image data to the coordinate system of the first reconstructed image data to generate a re-sampled non-attenuation-corrected reconstructed image data corresponding to the second imaging modality.

In one exemplary embodiment, the computer component uses the registration information to re-orient the attenuation-corrected reconstructed image data to generate a re-oriented attenuation-corrected reconstructed image data corresponding to the second imaging modality, and uses the registration information to re-orient the non-attenuation-corrected image data to generate a re-oriented non-attenuation-corrected reconstructed image data corresponding to the second imaging modality. In one exemplary embodiment, the re-oriented attenuation-corrected reconstructed image data is one of a short axis image, a horizontal long axis image, a vertical long axis image, an oblique transverse image, an oblique sagittal image, and an oblique coronal image, and the re-oriented non-attenuation-corrected reconstructed image data is one of a short axis image, a horizontal long axis image, a vertical long axis image, an oblique transverse image, an oblique sagittal image, and an oblique coronal image.

In one exemplary embodiment, the computer component fuses the re-sampled attenuation-corrected reconstructed image data with the first reconstructed image data to form a first fused image data, and fuses the re-sampled non-attenuation-corrected reconstructed image data with the first reconstructed image data to form a second fused image data. In one exemplary embodiment, the computer component fuses the re-oriented attenuation-corrected reconstructed image data with the first reconstructed image data to form a first fused image data, and fuses the re-oriented non-attenuation-corrected reconstructed image data with the first reconstructed image data to form a second fused image data.

An image processing system according to one exemplary embodiment, includes means for inputting SPECT projection data, a SPECT transverse volume image without attenuation correction, a CT volume image, an attenuation map derived from reconstruction of the SPECT transverse volume image from the SPECT projection data, and registration information derived from registration of the SPECT transverse volume image to the CT volume image. The image processing system also includes means for reconstructing a SPECT transverse volume image with attenuation correction using the attenuation map and the registration information. The image processing system also includes means for registering the SPECT transverse volume image with attenuation correction and the CT volume image using the registration information. The registration information is stored in, carried by, or otherwise communicated through the attenuation map.

An image processing method according to one exemplary embodiment, includes generating a first tomographic projection data with a first imaging modality (e.g., a CT system), generating a second tomographic projection data with a second imaging modality (e.g., a SPECT or PET system), generating a first reconstructed image data from the first tomographic projection data, and generating a second reconstructed image data from the second tomographic projection data. The method further includes registering the second reconstructed image data with the first reconstructed image data to obtain an attenuation map and a registration information. The method includes using the second tomographic projection data, the attenuation map, and the registration information to generate an attenuation-corrected reconstructed image data corresponding to the second imaging modality, and using the second tomographic projection data and the registration information to generate a non-attenuation-corrected reconstructed image data corresponding to the second imaging modality.

In one exemplary embodiment, the method includes using the registration information to re-sample the attenuation-corrected reconstructed image data to a coordinate system of the first reconstructed image data to generate a re-sampled attenuation-corrected reconstructed image data corresponding to the second imaging modality, and using the registration information to re-sample the non-attenuation-corrected reconstructed image data to a coordinate system of the first reconstructed image data to generate a re-sampled non-attenuation-corrected reconstructed image data corresponding to the second imaging modality.

In one exemplary embodiment, the method includes using the registration information to re-orient the attenuation-corrected reconstructed image data to generate a re-oriented attenuation-corrected reconstructed image data corresponding to the second imaging modality, and using the registration information to re-orient the non-attenuation-corrected reconstructed image data to generate a re-oriented non-attenuation-corrected reconstructed image data corresponding to the second imaging modality. In one exemplary embodiment, the re-oriented attenuation-corrected reconstructed image data is one of a short axis image, a horizontal long axis image, a vertical long axis image, an oblique transverse image, an oblique sagittal image, and an oblique coronal image, and the re-oriented non-attenuation-corrected reconstructed image data is one of a short axis image, a horizontal long axis image, a vertical long axis image, an oblique transverse image, an oblique sagittal image, and an oblique coronal image.

In one exemplary embodiment, the re-sampled attenuation-corrected reconstructed image data is fused with the first reconstructed image data to form a first fused image data, and the re-sampled non-attenuation-corrected reconstructed image data is fused with the first reconstructed image data to form a second fused image data. In one exemplary embodiment, the re-oriented attenuation-corrected reconstructed image data is fused with the first reconstructed image data to form a first fused image data, and the re-oriented non-attenuation-corrected reconstructed image data is fused with the first reconstructed image data to form a second fused image data.

In view of the above, the attenuation-corrected reconstructed image data and the non-attenuation-corrected reconstructed image data, the re-sampled attenuation-corrected reconstructed image data and the re-sampled non-attenuation-corrected reconstructed image data, the re-oriented attenuation-corrected reconstructed image data and the re-oriented non-attenuation-corrected reconstructed image data, and/or the first fused image data and the second fused image data: are voxel-to-voxel aligned with one another, are both registered to the coordinate system of the second image data, and both conform to the DICOM standard.

Accordingly, the systems and the methods, along with the associated workflows, facilitate the direct one-to-one comparison of fused SPECT/CT images, with attenuation correction and without attenuation correction, for both transverse and re-oriented images. Furthermore, because the fused SPECT/CT images, with attenuation correction and without attenuation correction, for both transverse and re-oriented images, conform to the DICOM standard, these images can be displayed, processed, or otherwise utilized by applications supporting the DICOM file format.

Still further advantages, features, and/or aspects of the general inventive concepts will become more readily apparent from the following detailed description of exemplary embodiments, from the claims and from the accompanying drawings.

The invention may take form in various components and arrangements of components, and in various steps and arrangements of steps. The drawings are only for purposes of illustrating the preferred embodiments and are not to be construed as limiting the invention.

Figure 1B:
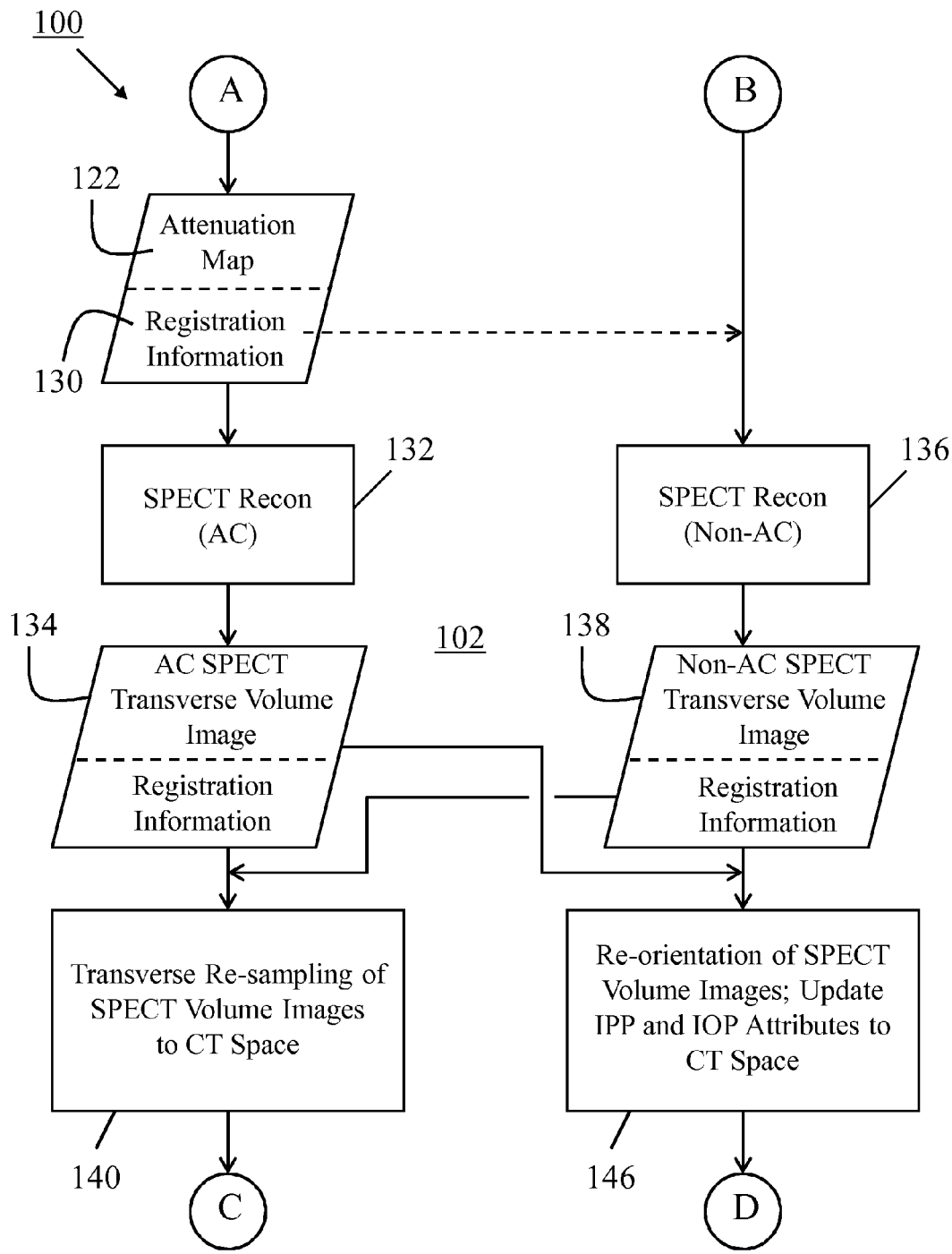
Figure 1C:
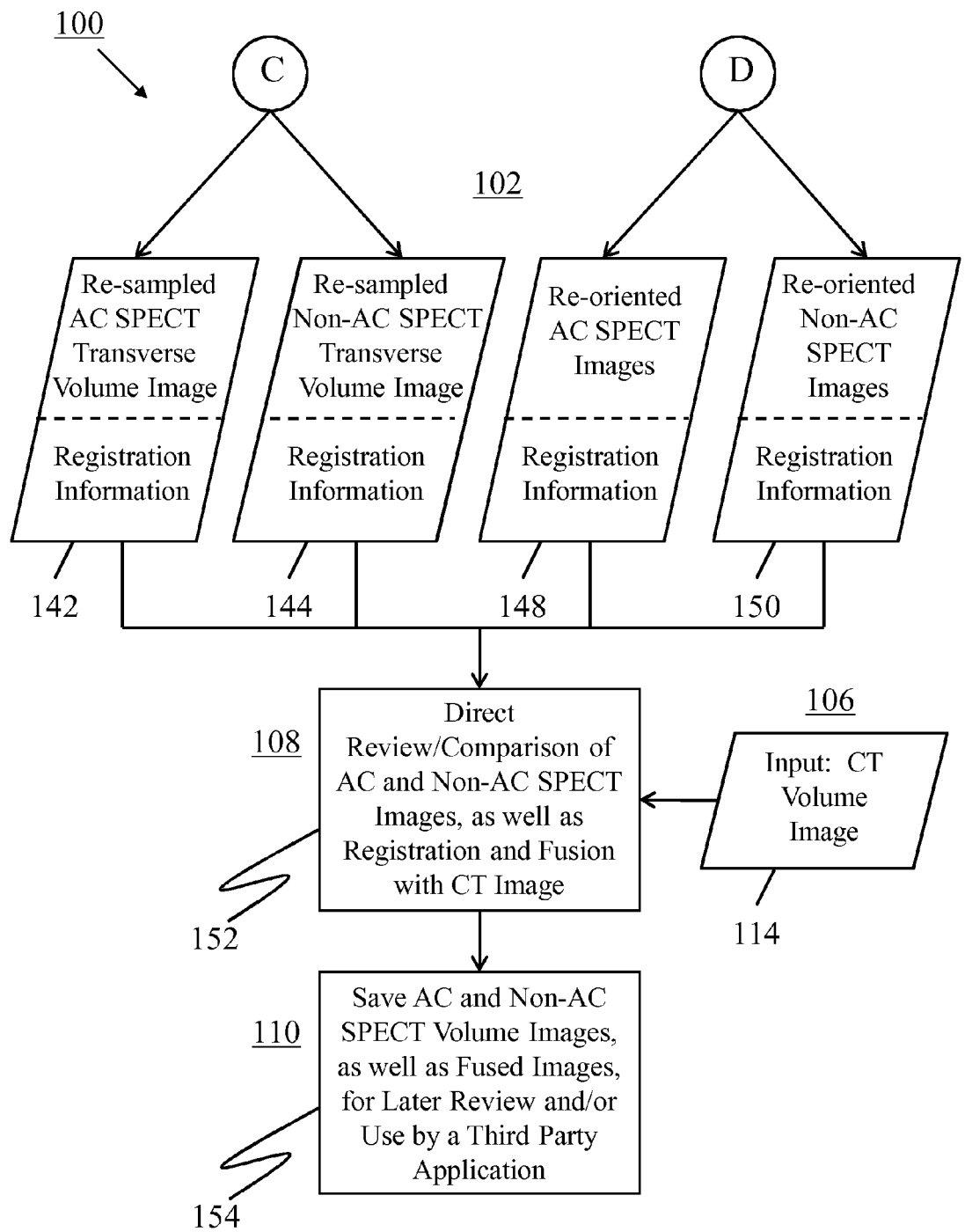

FIGS. 1A-1C form a flowchart illustrating image processing workflow in a hybrid SPECT/CT dual-modality system, according to one exemplary embodiment.

Figure 2A:
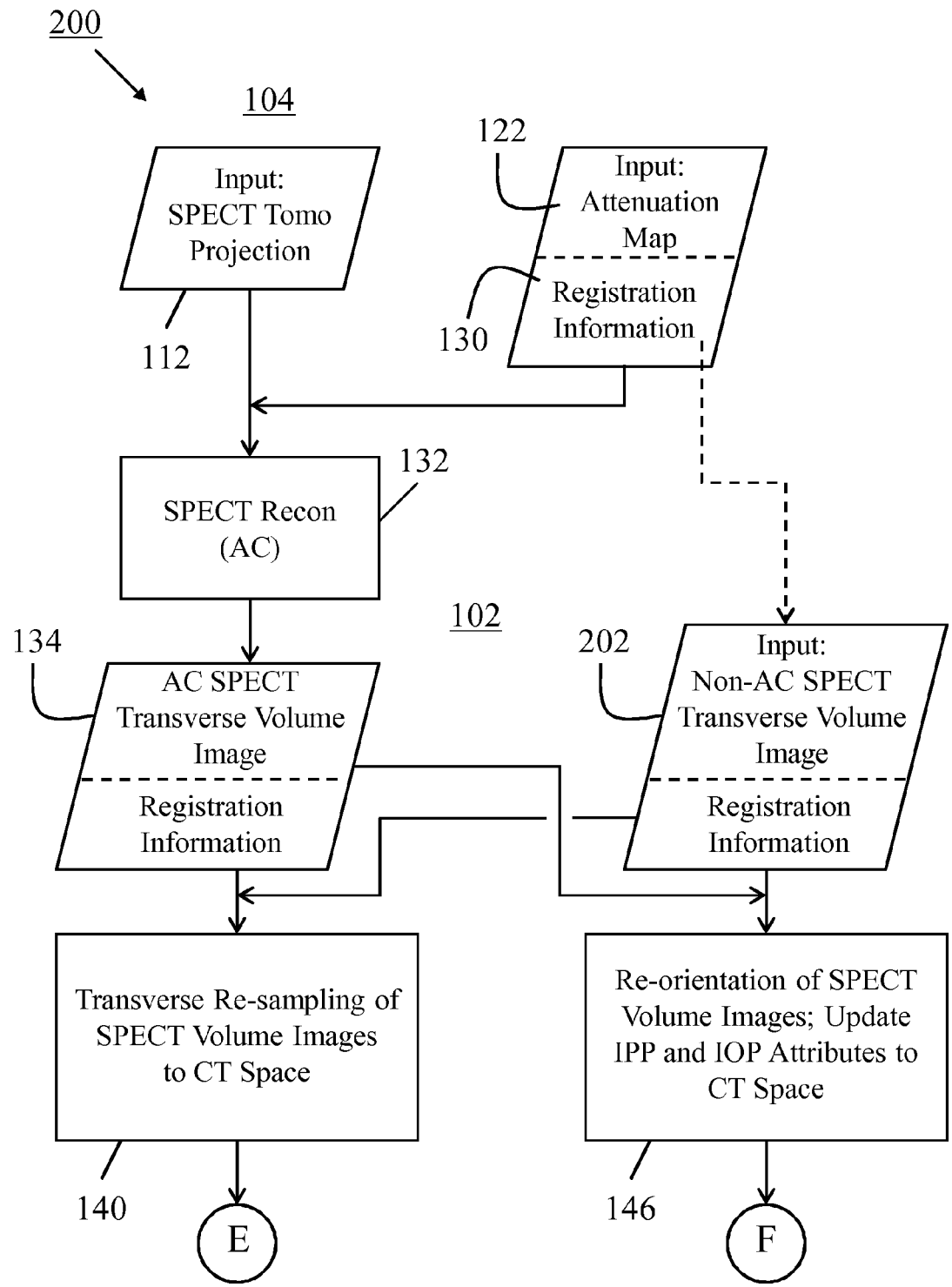
Figure 2B:
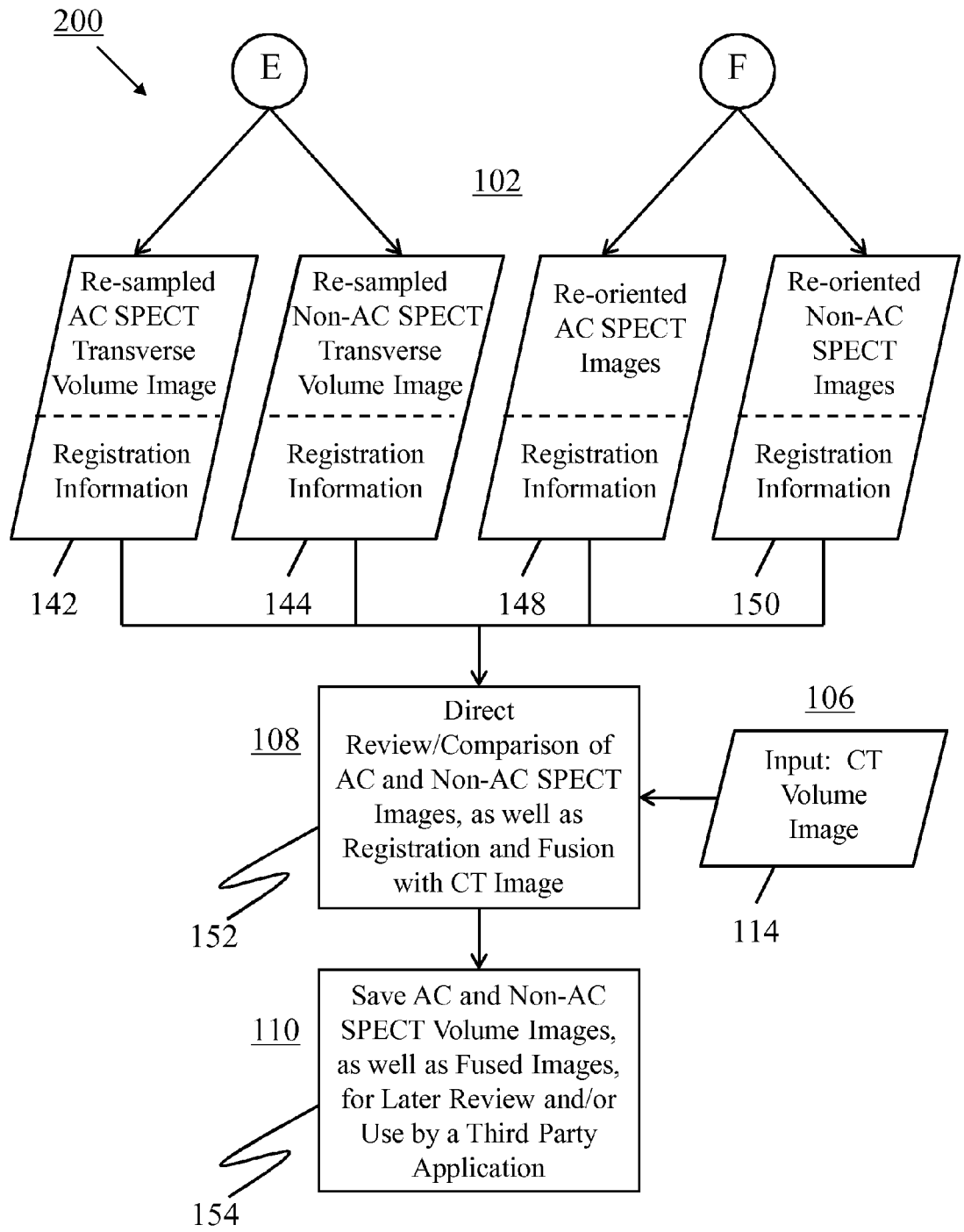

FIGS. 2A-2B form a flowchart illustrating image processing workflow in a hybrid SPECT/CT dual-modality system, according to one exemplary embodiment.

Figure 3A:
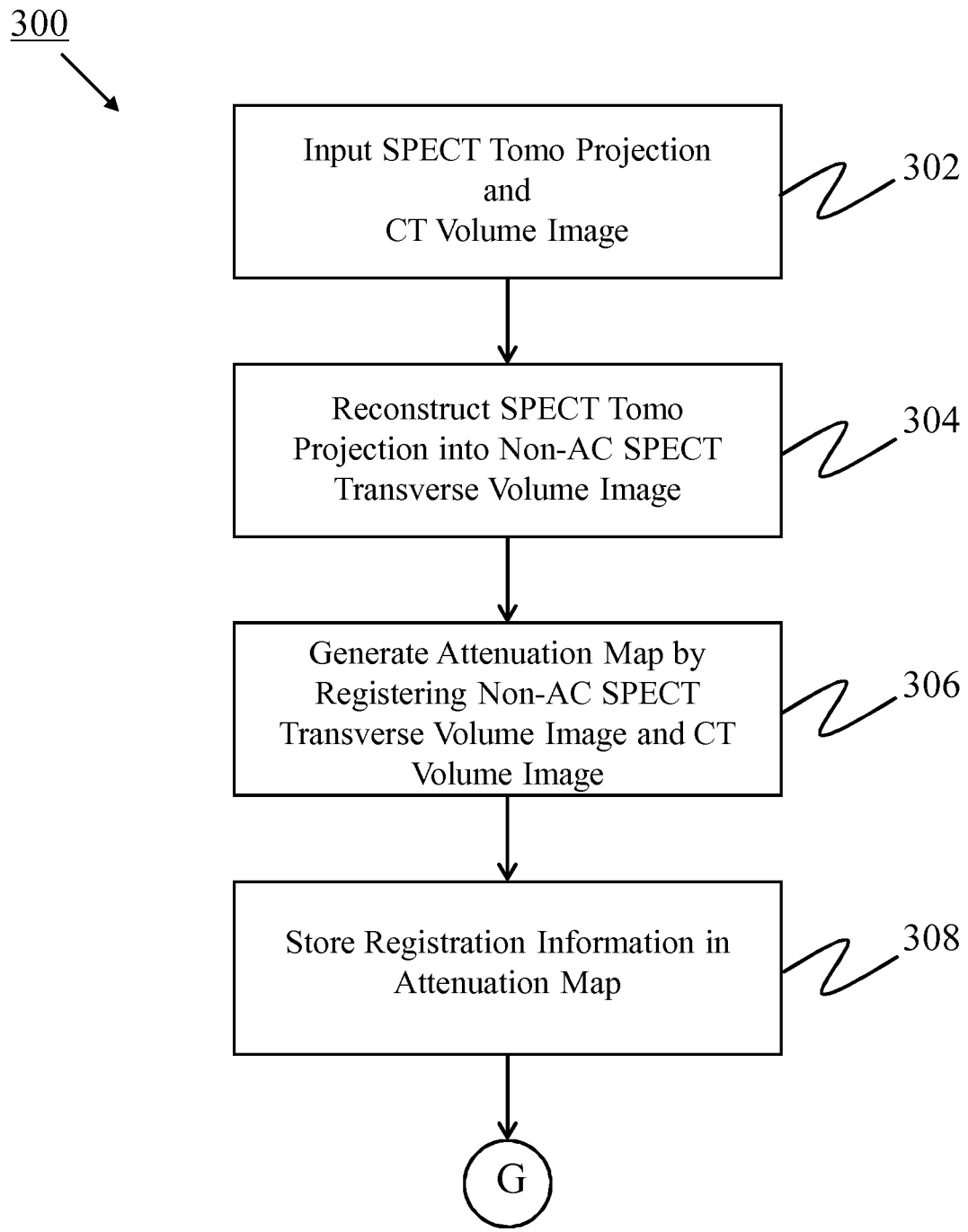
Figure 3B:
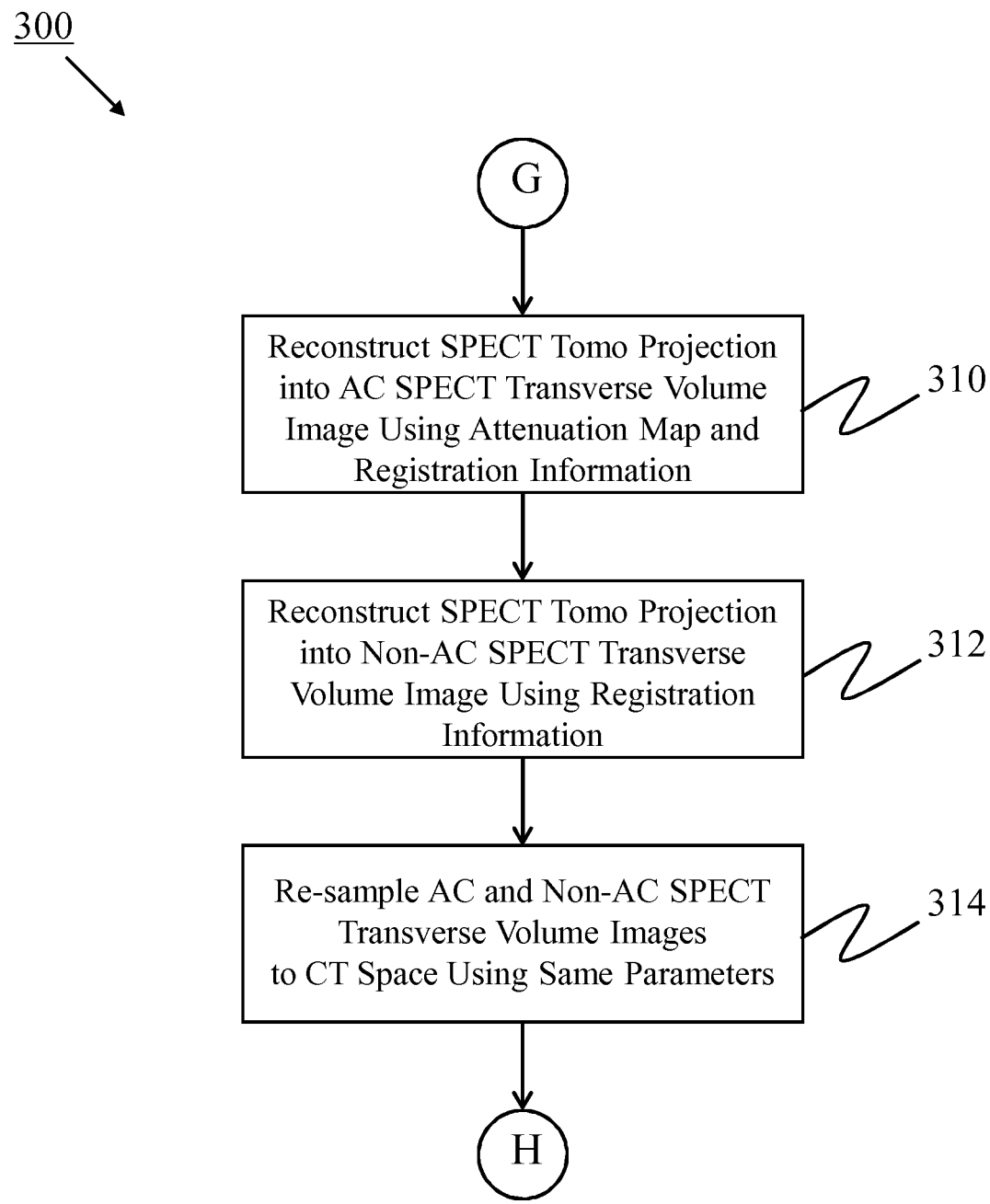
Figure 3C:
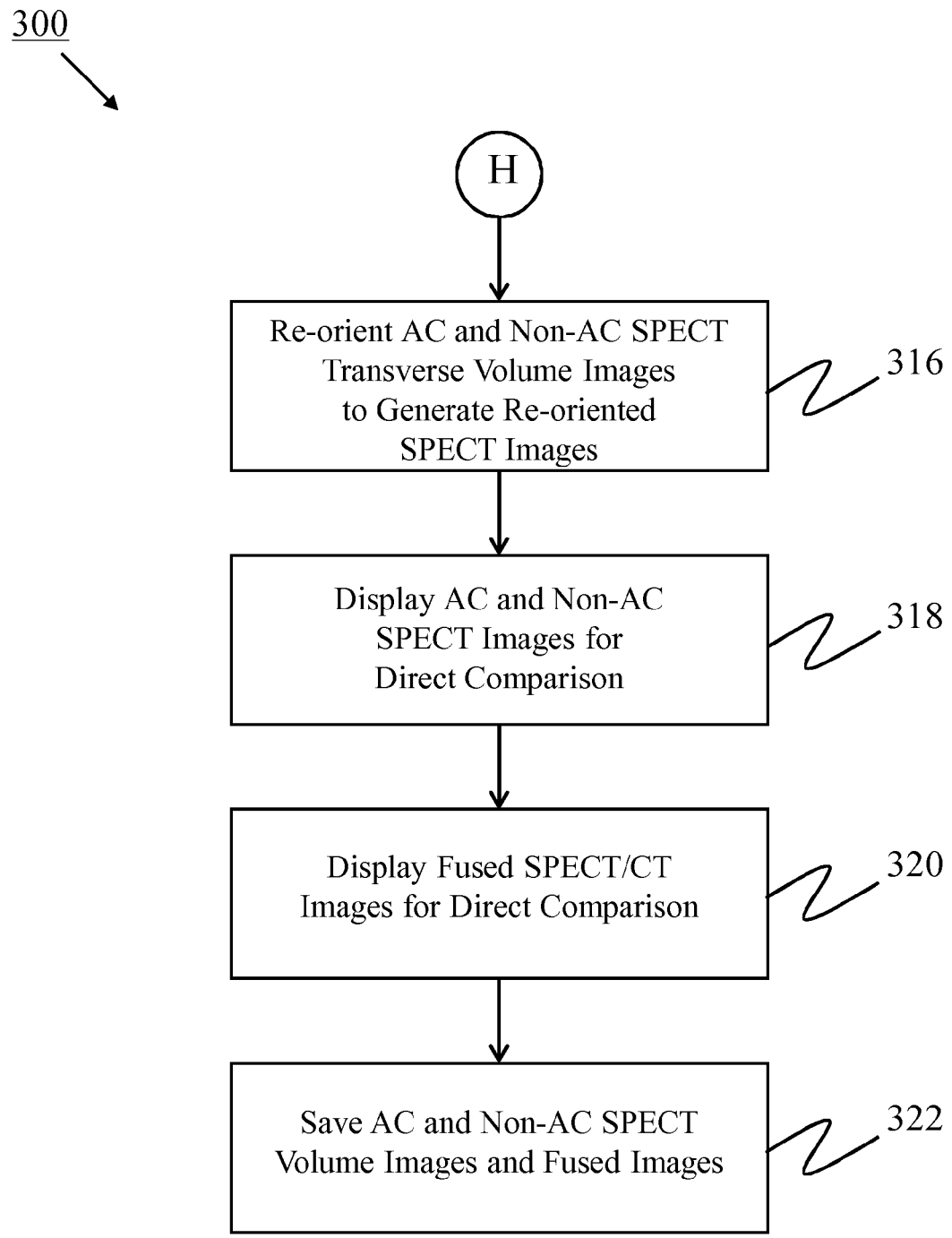

FIGS. 3A-3C form a flow chart illustrating a hybrid SPECT/CT dual-modality imaging method, according to one exemplary embodiment.

Figure 4A:
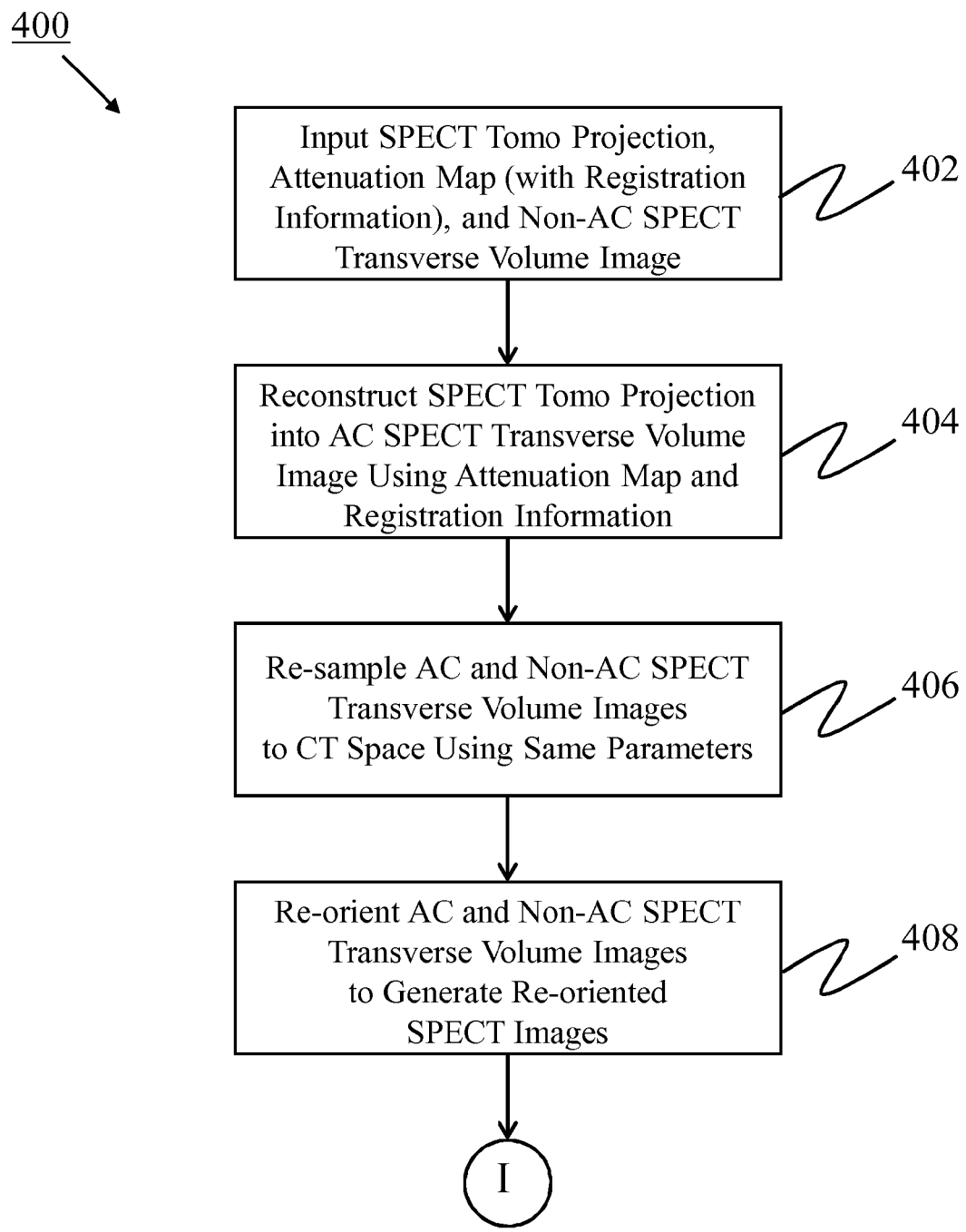
Figure 4B:
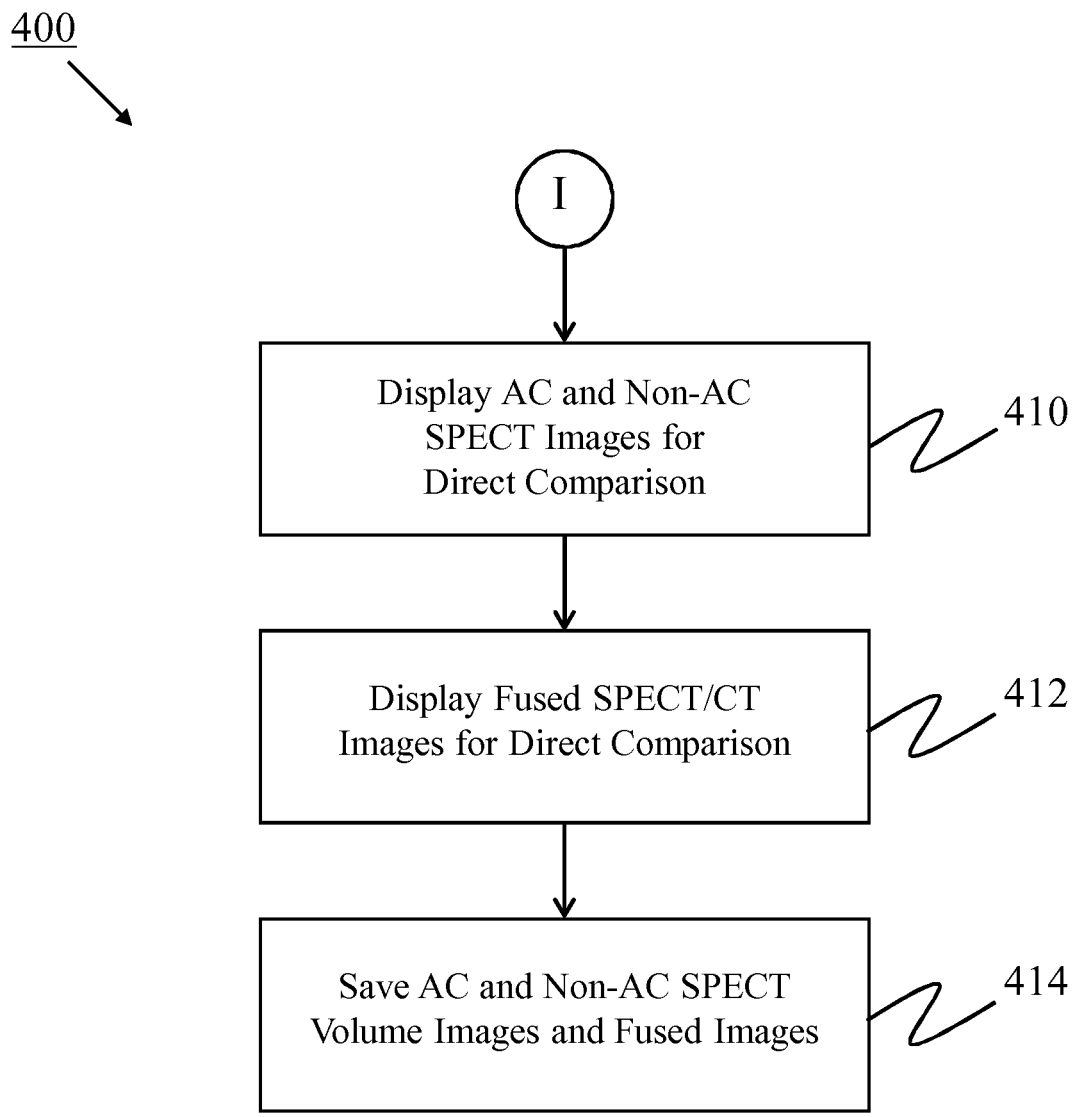

FIGS. 4A-4B form a flow chart illustrating a hybrid SPECT/CT dual-modality imaging method, according to one exemplary embodiment.

While the general inventive concepts are susceptible of embodiment in many different forms, there are shown in the drawings and will be described herein in detail specific embodiments thereof with the understanding that the present disclosure is to be considered as an exemplification of the principles of the general inventive concepts. Accordingly, the general inventive concepts are not intended to be limited to the specific embodiments illustrated herein.

The various needs or desires of users utilizing a SPECT/CT imaging system or method may conflict with one another. For example, when CT-based AC is applied, the IPP and IOP attributes of a reconstructed transverse SPECT image can be calculated relative to the CT patient space coordinate system, which builds a link of registration between the AC SPECT image and the CT image. However, because it is very common to have re-orientations involved in the registration, the new IOP of the re-oriented transverse SPECT image in the CT space typically is no longer the vector value [1 0 0 0 1 0]. Because this contradicts with the definition of transverse volume images as set forth in the DICOM standard, the transverse image data could be rejected by some DICOM applications.

As a partial solution to this problem, re-sampling of an AC SPECT image to the CT space could be performed so that the AC SPECT image and the CT image are explicitly registered and adhere to the definitions of the DICOM standard (such as having a vector value of [1 0 0 0 1 0] for the transverse IOP attribute). However, there is no convenient corresponding registration information for the non-AC data of a non-AC SPECT image. Therefore, the non-AC SPECT data are not readily re-sampled and, thus, are often left as un-re-sampled. As a result, the non-AC SPECT image is not registered to the CT image, and also is no longer voxel-to-voxel aligned with the re-sampled AC SPECT image. This prevents the ability to perform a meaningful direct one-to-one comparison between the non-AC SPECT image and re-sampled AC SPECT image, not to mention the ability to fuse the SPECT images with the CT image and perform a meaningful direct one-to-one comparison.

As another approach, an off-line re-sampling of the non-AC data of a SPECT image to the CT space could be performed. However, this off-line re-sampling would likely differ from the re-sampling process applied to the AC data of the SPECT image, especially when manual adjustments by a user are involved during registration. Additionally, this approach could lead to a broken workflow and sacrifice overall user convenience.

In view of the above, these competing needs and desires of users can be addressed in image processing workflows. The exemplary embodiments set forth below relate to new and improved hybrid SPECT/CT image processing systems and methods, along with their related workflows, that satisfy these various needs or desires for fusion display of CT and SPECT images, whether AC or non-AC, for both transverse and reoriented images.

A hybrid SPECT/CT dual-modality system, according to one exemplary embodiment, includes one or more computer components for processing SPECT and CT data. As used herein, "computer component" includes, but is not limited to, a computer-related entity, either hardware, firmware, software, a combination thereof, or software in execution. For example, a computer component can be, but is not limited to being, a processor, an object, an executable, a process running on a processor, a thread of execution, a program and a computer. By way of illustration, both an application running on a server computer and the server computer can be computer components. One or more computer components can reside within a process or thread of execution and a computer component can be localized on one computer or distributed between two or more computers. When "computer component" refers to a computer, it can also encompass various peripherals (e.g., input devices, data storage devices, display devices, and so on) for interfacing with the computer.

The hybrid SPECT/CT dual-modality system can also include logic implemented by or interfaced with the computer components. As used herein, "logic" includes, but is not limited to, hardware, firmware, software or combinations of each to perform a function or an action, or to cause a function or action to be performed by another component. For example, based on a desired application or need, logic may include a software controlled microprocessor, discrete logic such as an application specific integrated circuit (ASIC), or other programmed logic device. Logic may also be fully embodied as software.

In the hybrid SPECT/CT dual-modality system 100, a computer component 102 is interfaced or otherwise in data communication with a SPECT data input device 104, a CT data input device 106, a display device 108 (e.g., one or more monitors), and a data storage device 110. In one exemplary embodiment, the SPECT data input device 104 and the CT data input device 106 are integrated or fixed relative to one another. Each of the SPECT data input device 104 and the CT data input device 106 can store its respective data to the data storage device 110 for subsequent retrieval by the computer component 102.

The image processing workflow corresponding to the hybrid SPECT/CT dual-modality system 100 is shown in FIGS. 1A-1C. In accordance with this workflow, SPECT tomographic projection data 112 and a CT volume image 114 are input to the system 100. The CT volume image 114 is previously derived from a reconstruction of CT tomographic projection data. The SPECT tomographic projection data 112 can be input, for example, from the SPECT data input device 104 or the data storage device 110. The CT volume image 114 can be input, for example, from the CT data input device 106 or the data storage device 110. Initial reconstruction logic 116 performs a reconstruction of the SPECT tomographic projection data 112 without AC to generate a non-AC SPECT transverse volume image 118.

Registration logic 120 registers the non-AC SPECT transverse volume image 118 and the CT volume image 114 to generate an attenuation map 122 (see FIGS. 1A and 1B). The registration logic 120 can include one or more of parameter-based registration logic 124, manual adjustment registration logic 126, and auto image-based registration logic 128. The parameter-based registration logic 124 can, for example, register the images based on the geometry of the dual-modality system (e.g., the SPECT data input device 104 and the CT data input device 106), such as the distance a common patient table is linearly translated to move between the devices. The manual adjustment registration logic 126 can, for example, register the images based on a user's manual adjustments or movements of one image relative to the other image in a fusion view on a display device 108. The auto image-based registration logic 128 can, for example, apply a software-based matching algorithm to register the images using values in the images themselves, such as through cross-correlation, local-correlation, etc.

Registration information 130 from the registration logic 120, such as information on the parameter-based registration, manual adjustment registration, and/or auto image-based registration, is saved in, carried by, or otherwise communicated through the attenuation map 122. The registration information 130 can be saved or carried, for example, in a combination of both public (e.g., the IPP and the IOP) and private attributes in the header of the DICOM file corresponding to the attenuation map 122. In this manner, the registration information 130 in the attenuation map 122 serves as a bridge to link the geometric relationship between the SPECT and CT images.

The computer component 102 then uses AC SPECT reconstruction logic 132 and the attenuation map 122 including the registration information 130 to perform AC SPECT reconstruction of the SPECT tomographic projection data 112. The output of the AC SPECT reconstruction is an AC SPECT transverse volume image 134.

The computer component 102 also uses non-AC SPECT reconstruction logic 136 and the registration information 130 (provided by or obtained from the attenuation map 122) to perform non-AC SPECT reconstruction of the SPECT tomographic projection data 112. The output of the non-AC SPECT reconstruction is a non-AC SPECT transverse volume image 138.

In one exemplary embodiment, the AC SPECT reconstruction and the non-AC SPECT reconstruction are performed in parallel or otherwise at the same time. In this manner, the registration information 130 carried by the attenuation map 122 can be shared by both reconstructions even though attenuation correction is not applied to the non-AC SPECT reconstruction. Additionally, the registration information 130 is passed to the output of the reconstructions, i.e., the AC SPECT transverse volume image 134 and the non-AC SPECT transverse volume image 138.

The computer component 102 uses re-sampling logic 140 to re-sample both the AC SPECT transverse volume image 134 and the non-AC SPECT transverse volume image 138 to the CT space. The output of the re-sampling of the AC SPECT transverse volume image 134 is a re-sampled AC SPECT transverse volume image 142. The output of the re-sampling of the non-AC SPECT transverse volume image 138 is a re-sampled non-AC SPECT transverse volume image 144. Because both the AC SPECT transverse volume image 134 and the non-AC SPECT transverse volume image 138 are re-sampled using the same parameters (e.g., the registration information 130), the re-sampled AC SPECT transverse volume image 142 and the re-sampled non-AC SPECT transverse volume image 144 are voxel-to-voxel aligned with one another, are both registered to the CT space, and both conform to the DICOM standard by having a vector value of [1 0 0 0 1 0] in their public IOP attributes.

The computer component 102 uses re-orientation logic 146 to reorient both the AC SPECT transverse volume image 134 and the non-AC SPECT transverse volume image 138 in the same way. The output of the reorientation logic 146 is one or more re-oriented AC SPECT images 148 and one or more re-oriented non-AC SPECT images 150. The re-oriented AC SPECT images 148 and/or the re-oriented non-AC SPECT images 150 can include, for example, a short axis image, a horizontal long axis image, a vertical long axis image, an oblique transverse image, an oblique sagittal image, and/or an oblique coronal image. For each of the re-oriented SPECT images, its public IOP and IPP attributes are updated to the CT space, so that each re-oriented SPECT image is registered to the CT image in the CT coordinate system, not voxel-to-voxel aligned with the CT image.

Thereafter, the computer component 102 can use the display device 108 to cause, facilitate or otherwise support display 152 of the same types (e.g., re-sampled, re-oriented) of AC and non-AC SPECT images. For example, the AC and non-AC SPECT images can be displayed 152 side by side for a meaningful direct one-to-one comparison of the images. Furthermore, both the AC and non-AC SPECT images can be fused with the CT volume image 114 for comparison of the fused images. The fused images can provide localization or otherwise enhance diagnosis.

Furthermore, the computer component 102 can use the data storage device 110 to cause, facilitate, or otherwise support saving 154 of the attenuation map 122 including the registration information 130, the re-sampled AC SPECT transverse volume image 142, the re-sampled non-AC SPECT transverse volume image 144, the re-oriented AC SPECT images 148, the re-oriented non-AC SPECT images 150, the fused SPECT/CT images to the data storage device 110, and/or other image data. Accordingly, the saved information and images 154 can be subsequently retrieved from the data storage device 110 for use or review, including use or review by a third-party application, a different application, a different computer component, or the like.

A hybrid SPECT/CT dual-modality system 200, according to another exemplary embodiment, includes one or more computer components (e.g., the computer component 102) for processing SPECT and CT data. The hybrid SPECT/CT dual-modality system 200 implements an image processing workflow similar to the image processing workflow corresponding to the hybrid SPECT/CT dual-modality system 100. Accordingly, like reference numbers are used where appropriate. However, as shown in FIGS. 2A-2B, in the image processing workflow for the system 200, a non-AC SPECT transverse volume image 202 was reconstructed previously and independently of either the CT volume image 114 or the CT-based attenuation map 122.

In accordance with this workflow, the non-AC SPECT transverse volume image 202, along with the SPECT tomographic projection data 112 and the attenuation map 122 including the registration information 130 (for AC reconstruction), are input to the system 200. The non-AC SPECT transverse volume image 202 and the attenuation map 122 can be input, for example, from the data storage device 110. The SPECT tomographic projection data 112 can be input, for example, from the SPECT data input device 104 or the data storage device 110.

In the system 200, because the attenuation map 122 was previously generated and the registration information 130 saved into the attenuation map 122, registration of the non-AC SPECT transverse volume image 118 and the CT volume image 114 (e.g., using registration logic 120) is not needed. Instead, the registration information 130 saved in the attenuation map 122 can be used during subsequent processing within the system 200. Because the re-sampling (e.g., using the re-sampling logic 140), re-orientation (e.g., using the re-orientation logic 146), and subsequent processing in the system 200 is the same as described above for the system 100, a separate discussion thereof is omitted here.

A hybrid SPECT/CT dual-modality method 300, according to one exemplary embodiment, will be described with references to FIGS. 3A-3C. In the hybrid SPECT/CT dual-modality method 300, SPECT tomographic projection data and a CT volume image are input in step 302. The SPECT tomographic projection data can be input, for example, from a SPECT scanner or a data storage device. The CT volume image can be input, for example, from a CT scanner or a data storage device. The SPECT tomographic projection data is initially reconstructed (without AC) to generate a non-AC SPECT transverse volume image in step 304.

The non-AC SPECT transverse volume image and the CT volume image are registered with one another to generate an attenuation map in step 306. The registration of the SPECT and CT images can include one or more of parameter-based registration, manual adjustment registration, and auto image-based registration. Registration information obtained during the registration process is stored in, carried by, or otherwise communicated through the attenuation map in step 308. The registration information can be stored, for example, in a combination of both public (e.g., the IPP and the IOP) and private attributes in the header of the DICOM file corresponding to the attenuation map. In this manner, the registration information in the attenuation map serves as a bridge to link the geometric relationship between the SPECT and CT images.

The attenuation map including the registration information is used to reconstruct the SPECT tomo projection data (with AC) into an AC SPECT transverse volume image in step 310. The registration information (received or otherwise obtained from the attenuation map) is used to reconstruct the SPECT tomographic projection data (without AC) into a non-AC SPECT transverse volume image in step 312. In one exemplary embodiment, the reconstructions in steps 310 and 312 are performed in parallel or otherwise at the same time. In this manner, the registration information carried by the attenuation map can be shared by both reconstructions even though attenuation correction is only applied in one of the reconstructions. Additionally, the registration information is passed to the output of the reconstructions, i.e., the AC SPECT transverse volume image and the non-AC SPECT transverse volume image.

Both the AC SPECT transverse volume image and the non-AC SPECT transverse volume image are re-sampled to the CT space in step 314. The output of the re-sampling of the AC SPECT transverse volume image is a re-sampled AC SPECT transverse volume image. The output of the re-sampling of the non-AC SPECT transverse volume image is a re-sampled non-AC transverse volume image. Because both the AC SPECT transverse volume image and the non-AC SPECT transverse volume image are re-sampled using the same parameters (e.g., the registration information from the attenuation map), the re-sampled AC SPECT transverse volume image and the re-sampled non-AC SPECT transverse volume image are voxel-to-voxel aligned with one another, are both registered to the CT space, and both conform to the DICOM standard by having a vector value of [1 0 0 0 1 0] in their public IOP attributes.

Both the AC SPECT transverse volume image and the non-AC SPECT transverse volume image are re-oriented in the same way in step 316. This re-orientation of the AC and non-AC SPECT transverse volume images forms different (i.e., re-oriented) AC and non-AC SPECT images, for example, a short axis image, a horizontal long axis image, a vertical long axis image, an oblique transverse image, an oblique sagittal image, and/or an oblique coronal image. For each of the re-oriented images, its public IOP and IPP attributes are updated to the CT space, so that each re-oriented image is registered to the CT image in the CT coordinate system, not voxel-to-voxel aligned with the CT image.

Thereafter, the method 300 supports the display of the same types (e.g., re-sampled, re-oriented) of AC and non-AC SPECT images in step 318. For example, the AC and non-AC SPECT images can be displayed side by side for a meaningful direct one-to-one comparison of the images. Furthermore, both the AC and non-AC SPECT images can be fused with the CT volume image and displayed for comparison of the fused images in step 320. The fused images can provide localization and/or otherwise enhance diagnosis.

Furthermore, the method 300 in step 322 supports saving the generated images and information (e.g., to a data storage device) for later retrieval. The images and information that are saved can include, for example, the attenuation map including the registration information, the re-sampled AC SPECT transverse volume image, the re-sampled non-AC SPECT transverse volume image, the re-oriented AC SPECT images, the re-oriented non-AC SPECT images, and/or the fused SPECT/CT images. In this manner, the images and information can be retrieved and used at anytime for review by a third-party application, a different application, a different computer component, or the like.

A hybrid SPECT/CT dual-modality method 400, according to one exemplary embodiment, will be described with reference to FIGS. 4A-4B. The hybrid SPECT/CT dual-modality method 400 is similar to the hybrid SPECT/CT dual-modality method 300. Accordingly, like reference numbers are used where appropriate. However, as shown in FIGS. 4A-4B, in the hybrid SPECT/CT dual-modality method 400, a non-AC SPECT transverse volume image was reconstructed previously and independently of either the CT volume image or the CT-based attenuation map. Additionally, the CT volume image was reconstructed previously from CT tomographic projection data.

In accordance with this method 400, the non-AC SPECT transverse volume image, along with the SPECT tomographic projection data and the attenuation map including the registration information (for AC reconstruction), are input in step 402. The non-AC SPECT transverse volume image and the attenuation map can be input, for example, from a data storage device. The SPECT tomographic projection data can be input, for example, from a SPECT scanner or the data storage device.

In the method 400, because the attenuation map was previously generated and the registration information saved into the attenuation map, registration of the non-AC SPECT transverse volume image and the CT volume image is not needed. Instead, the registration information saved in the attenuation map can be used during subsequent steps in the method 400. Because the re-sampling, re-orientation, and subsequent processing in the method 400 is the same as described above for the method 300, a separate discussion thereof is omitted here.

In view of the above, hybrid SPECT/CT dual-modality systems and methods facilitate obtaining, displaying, storing, and otherwise utilizing valuable physiological and anatomical information. In accordance with these systems and methods, registration and fusion display of the SPECT and the CT images can simplify identification and localization of suspected defects or tumors for diagnosis. Because the systems and methods insure the images adhere to the DICOM standard, the images can readily be reviewed using third party software. Additionally, the systems and methods allow users to perform direct one-to-one comparisons between the SPECT images reconstructed both with AC and without AC, for both transverse and re-oriented images.

The above description of specific embodiments has been given by way of example. From the disclosure given, those skilled in the art will not only understand the general inventive concepts and any attendant advantages, but will also find apparent various changes and modifications to the structures and methods disclosed. For example, while discussed herein in the context of SPECT/CT multi-modality imaging, the general inventive concepts could be applied to other types of multi-modality imaging, such as PET/CT, SPECT/MR, PET/MR, and so on. It is sought, therefore, to cover all such changes and modifications as fall within the spirit and scope of the general inventive concepts, as defined by the appended claims, and equivalents thereof.

What is claimed is:

1. An image processing system, the system comprising:
   a computer,
   a first tomographic projection data generated by a first imaging modality, and a second tomographic projection data generated by a second imaging modality,
   wherein the computer generates a first reconstructed image data from the first tomographic projection data, and a second reconstructed image data from the second tomographic projection data,
   wherein the computer registers the second reconstructed image data with the first reconstructed image data to generate an attenuation map and a registration information,
   wherein the computer uses the second tomographic projection data, the attenuation map, and the registration information to generate an attenuation-corrected reconstructed image data corresponding to the second imaging modality, and
   wherein the computer uses the second tomographic projection data and the registration information to generate a non-attenuation-corrected reconstructed image data corresponding to the second imaging modality.

2. The system of claim 1, wherein the attenuation-corrected reconstructed image data and the non-attenuation-corrected reconstructed image data are voxel-to-voxel aligned with one another,
   wherein the attenuation-corrected reconstructed image data and the non-attenuation-corrected reconstructed image data are both registered to a coordinate system of the first reconstructed image data, and
   wherein the attenuation-corrected reconstructed image data and the non-attenuation-corrected reconstructed image data both conform to a DICOM standard.

3. The system of claim 1, wherein the computer uses the registration information to re-sample the attenuation-corrected reconstructed image data to a coordinate system of the first reconstructed image data to generate a re-sampled attenuation-corrected reconstructed image data corresponding to the second imaging modality, and
   wherein the computer uses the registration information to re-sample the non-attenuation-corrected reconstructed image data to the coordinate system of the first reconstructed image data to generate a re-sampled non-attenuation-corrected reconstructed image data corresponding to the second imaging modality.

4. The system of claim 3, wherein the re-sampled attenuation-corrected reconstructed image data and the re-sampled non-attenuation-corrected reconstructed image data are voxel-to-voxel aligned with one another,
   wherein the re-sampled attenuation-corrected reconstructed image data and the re-sampled non-attenuation-corrected reconstructed image data are both registered to a coordinate system of the first reconstructed image data, and
   wherein the re-sampled attenuation-corrected reconstructed image data and the re-sampled non-attenuation-corrected reconstructed image data both conform to a DICOM standard.

5. The system of claim 3, wherein the re-sampled attenuation-corrected reconstructed image data is fused with the first reconstructed image data to form a first fused image data, and
   wherein the re-sampled non-attenuation-corrected reconstructed image data is fused with the first reconstructed image data to form a second fused image data.

6. The system of claim 5, further comprising a display device in data communication with the computer, wherein the computer is operable to cause at least one of:
   the attenuation-corrected reconstructed image data and the non-attenuation-corrected reconstructed image data, or
   the re-sampled attenuation-corrected reconstructed image data and the re-sampled non-attenuation-corrected reconstructed image data, or
   the first fused image data and the second fused image data,
   to be displayed on the display device at the same time.

7. The system of claim 5, further comprising a data storage device in data communication with the computer, wherein the computer is operable to cause at least one of the attenuation map, the registration information, the attenuation-corrected reconstructed image data, the non-attenuation-corrected reconstructed image data, the re-sampled attenuation-corrected reconstructed image data, the re-sampled non-attenuation-corrected reconstructed image data, the first fused image data, and the second fused image data, to be stored on the data storage device.

8. The system of claim 5, wherein the first fused image data and the second fused image data are voxel-to-voxel aligned with one another,
   wherein the first fused image data and the second fused image data are both registered to a coordinate system of the first reconstructed image data, and
   wherein the first fused image data and the second fused image data both conform to a DICOM standard.

9. The system of claim 1, wherein the computer uses the registration information to re-orient the attenuation-corrected reconstructed image data to generate a re-oriented attenuation-corrected reconstructed image data corresponding to the second imaging modality, and
   wherein the computer uses the registration information to re-orient the non-attenuation-corrected image data to generate a re-oriented non-attenuation-corrected reconstructed image data corresponding to the second imaging modality.

10. The system of claim 9, wherein the re-oriented attenuation-corrected reconstructed image data is one of a short axis image, a horizontal long axis image, a vertical long axis image, an oblique transverse image, an oblique sagittal image, and an oblique coronal image, and
    wherein the re-oriented non-attenuation-corrected reconstructed image data is one of a short axis image, a horizontal long axis image, a vertical long axis image, an oblique transverse image, an oblique sagittal image, and an oblique coronal image.

11. The system of claim 9, wherein the re-oriented attenuation-corrected reconstructed image data and the re-oriented non-attenuation-corrected reconstructed image data are voxel-to-voxel aligned with one another,
wherein the re-oriented attenuation-corrected reconstructed image data and the re-oriented non-attenuation-corrected reconstructed image data are both registered to a coordinate system of the first reconstructed image data, and
wherein the re-oriented attenuation-corrected reconstructed image data and the re-oriented non-attenuation-corrected reconstructed image data both conform to a DICOM standard.

12. The system of claim 9, wherein the re-oriented attenuation-corrected reconstructed image data is fused with the first reconstructed image data to form a first fused image data, and
wherein the re-oriented non-attenuation-corrected reconstructed image data is fused with the first reconstructed image data to form a second fused image data.

13. The system of claim 12, further comprising a display device in data communication with the computer, wherein the computer is operable to cause at least one of:
the attenuation-corrected reconstructed image data and the non-attenuation-corrected reconstructed image data, or
the re-oriented attenuation-corrected reconstructed image data and the re-oriented non-attenuation-corrected reconstructed image data, or
the first fused image data and the second fused image data, to be displayed on the display device at the same time.

14. The system of claim 12, further comprising a data storage device in data communication with the computer, wherein the computer is operable to cause at least one of the attenuation map, the registration information, the attenuation-corrected reconstructed image data, the non-attenuation-corrected reconstructed image data, the re-oriented attenuation-corrected reconstructed image data, the re-oriented non-attenuation-corrected reconstructed image data, the first fused image data, and the second fused image data, to be stored on the data storage device.

15. The system of claim 1, wherein the registration information is stored in the attenuation map.

16. An image processing method, the method comprising:
generating a first tomographic projection data with a first imaging modality, and generating a second tomographic projection data with a second imaging modality,
generating a first reconstructed image data from the first tomographic projection data, and generating a second reconstructed image data from the second tomographic projection data,
registering the second reconstructed image data with the first reconstructed image data to obtain an attenuation map and a registration information,
using the second tomographic projection data, the attenuation map, and the registration information to generate an attenuation-corrected reconstructed image data corresponding to the second imaging modality, and
using the second tomographic projection data and the registration information to generate a non-attenuation-corrected reconstructed image data corresponding to the second imaging modality.

17. The method of claim 16, wherein the attenuation-corrected reconstructed image data and the non-attenuation-corrected reconstructed image data are voxel-to-voxel aligned with one another,
wherein the attenuation-corrected reconstructed image data and the non-attenuation-corrected reconstructed image data are both registered to a coordinate system of the first reconstructed image data, and
wherein the attenuation-corrected reconstructed image data and the non-attenuation-corrected reconstructed image data both conform to a DICOM standard.

18. The method of claim 16, further comprising:
using the registration information to re-sample the attenuation-corrected reconstructed image data to a coordinate system of the first reconstructed image data to generate a re-sampled attenuation-corrected reconstructed image data corresponding to the second imaging modality, and
using the registration information to re-sample the non-attenuation-corrected reconstructed image data to a coordinate system of the first reconstructed image data to generate a re-sampled non-attenuation-corrected reconstructed image data corresponding to the second imaging modality.

19. The method of claim 18, wherein the re-sampled attenuation-corrected reconstructed image data and the re-sampled non-attenuation-corrected reconstructed image data are voxel-to-voxel aligned with one another,
wherein the re-sampled attenuation-corrected reconstructed image data and the re-sampled non-attenuation-corrected reconstructed image data are both registered to a coordinate system of the first reconstructed image data, and
wherein the re-sampled attenuation-corrected reconstructed image data and the re-sampled non-attenuation-corrected reconstructed image data both conform to a DICOM standard.

20. The method of claim 18, further comprising fusing the re-sampled attenuation-corrected reconstructed image data with the first reconstructed image data to form a first fused image data, and
fusing the re-sampled non-attenuation-corrected reconstructed image data with the first reconstructed image data to form a second fused image data.

21. The method of claim 20, further comprising displaying at the same time on a display device at least one of:
the attenuation-corrected reconstructed image data and the non-attenuation-corrected reconstructed image data, or
the re-sampled attenuation-corrected reconstructed image data and the re-sampled non-attenuation-corrected reconstructed image data, or
the first fused image data and the second fused image data.

22. The method of claim 20, further comprising storing on a data storage device at least one of the attenuation map, the registration information, the attenuation-corrected reconstructed image data, the non-attenuation-corrected reconstructed image data, the re-sampled attenuation-corrected reconstructed image data, the re-sampled non-attenuation-corrected reconstructed image data, the first fused image data, and the second fused image data.

23. The method of claim 20, wherein the first fused image data and the second fused image data are voxel-to-voxel aligned with one another,
wherein the first fused image data and the second fused image data are both registered to a coordinate system of the first reconstructed image data, and
wherein the first fused image data and the second fused image data both conform to a DICOM standard.

24. The method of claim 16, further comprising:
using the registration information to re-orient the attenuation-corrected reconstructed image data to generate a re-oriented attenuation-corrected reconstructed image data corresponding to the second imaging modality, and
using the registration information to re-orient the non-attenuation-corrected reconstructed image data to generate a re-oriented non-attenuation-corrected reconstructed image data corresponding to the second imaging modality.

25. The method of claim 24, wherein the re-oriented attenuation-corrected reconstructed image data is one of a short axis image, a horizontal long axis image, a vertical long axis image, an oblique transverse image, an oblique sagittal image, and an oblique coronal image, and
wherein the re-oriented non-attenuation-corrected reconstructed image data is one of a short axis image, a horizontal long axis image, a vertical long axis image, an oblique transverse image, an oblique sagittal image, and an oblique coronal image.

26. The method of claim 24, wherein the re-oriented attenuation-corrected reconstructed image data and the re-oriented non-attenuation-corrected reconstructed image data are voxel-to-voxel aligned with one another,
wherein the re-oriented attenuation-corrected reconstructed image data and the re-oriented non-attenuation-corrected reconstructed image data are both registered to a coordinate system of the first reconstructed image data, and
wherein the re-oriented attenuation-corrected reconstructed image data and the re-oriented non-attenuation-corrected reconstructed image data both conform to a DICOM standard.

27. The method of claim 24, wherein the re-oriented attenuation-corrected reconstructed image data is fused with the first reconstructed image data to form a first fused image data, and
wherein the re-oriented non-attenuation-corrected reconstructed image data is fused with the first reconstructed image data to form a second fused image data.

28. The method of claim 27, further comprising displaying at the same time on a display device at least one of:
the attenuation-corrected reconstructed image data and the non-attenuation-corrected reconstructed image data, or
the re-oriented attenuation-corrected reconstructed image data and the re-oriented non-attenuation-corrected reconstructed image data, or
the first fused image data and the second fused image data.

29. The method of claim 28, further comprising storing on a data storage device at least one of the attenuation map, the registration information, the attenuation-corrected reconstructed image data, the non-attenuation-corrected reconstructed image data, the re-oriented attenuation-corrected reconstructed image data, the re-oriented non-attenuation-corrected reconstructed image data, the first fused image data, and the second fused image data.

30. The method of claim 16, wherein the registration information is stored in the attenuation map.

31. A method of generating an attenuation map for correcting for attenuation during imaging, the method comprising:
inputting a first tomographic projection data generated by a first imaging modality, and a second tomographic projection data generated by a second imaging modality;
generating a first reconstructed image data from the first tomographic projection data, and a second reconstructed image data from the second tomographic projection data;
registering the second reconstructed image data with the first reconstructed image data to generate an attenuation map and a registration information;
embedding the registration information in the attenuation map; and
storing the attenuation map including the registration information on a computer readable medium.

32. The method of claim 31, wherein the attenuation map is stored as a file corresponding to the DICOM standard, and
wherein the registration information is stored a header portion of the file.

* * * * *